(12) United States Patent
Seppälä et al.

(10) Patent No.: US 7,186,759 B2
(45) Date of Patent: Mar. 6, 2007

(54) BIOLOGICALLY ACTIVE MATERIAL

(75) Inventors: Jukka Veli Seppälä, Helsinki (FI); Riitta Minna Hannele Malin, Helsinki (FI)

(73) Assignee: Vivoxid Oy, Turku (FI)

( * ) Notice: Subject to any disclaimer, the term of this patent is extended or adjusted under 35 U.S.C. 154(b) by 224 days.

(21) Appl. No.: 10/333,403

(22) PCT Filed: Jul. 12, 2001

(86) PCT No.: PCT/FI01/00664

§ 371 (c)(1),
(2), (4) Date: Jan. 21, 2003

(87) PCT Pub. No.: WO02/08320

PCT Pub. Date: Jan. 31, 2002

(65) Prior Publication Data

US 2004/0006153 A1    Jan. 8, 2004

(30) Foreign Application Priority Data

Jul. 21, 2000    (FI) .................................. 20001696

(51) Int. Cl.
*A61F 2/00*    (2006.01)
(52) U.S. Cl. ........................ 523/113; 523/114; 523/115; 524/414; 524/417
(58) Field of Classification Search ............... 523/113, 523/114, 115; 524/414, 417
See application file for complete search history.

(56) References Cited

U.S. PATENT DOCUMENTS 5,626,861 A * 5/1997 Laurencin et al. .......... 424/426

* cited by examiner

*Primary Examiner*—Edward J. Cain
(74) *Attorney, Agent, or Firm*—Kubovcik & Kubovcik

(57) ABSTRACT

The invention relates to a heterophasic composition which essentially consists of three immniscible components, A, B and C, and the production method of the same. The component A is some body compatible polymer, the component H is a water soluble or hydrolytically degradable substance which produces cavities or network like porosity after disappearing through solubilization or degradation, and a bioactive substance C which at least component B contains in form of particles as a blend component and which still exists in the pores or their walls after the degradation or solubilization of the component B. The materials according to the invention are biocompatible, solid in normal temperatures, mechanically processable, and thermally mouldable as well as bioactive in the sense that they have the capability to renew different kinds of tissues in the body, on the surface of the living organisms, in the cavities of the body and in the tissue engineering conditions outside the body, and that they can be used in tissue engineering, in tissue regeneration, in healing of damaged or lacking tissues, in tissue guiding when treating deficiencies, in controlled drug release, in the treatment methods of dentistry, in orthopedics and in plastic surgery.

6 Claims, 3 Drawing Sheets

BIOLOGICALLY ACTIVE MATERIAL

During the last years in the biomedical applications synthetic implant materials have been taken into use to an ever-increasing degree. Biomaterial is defined to be a synthetic structural material whose aim is to interact with the biological system, and to replace, to treat, promote healing and renewal of and to join tissue, organs or some function of the body. Applications of these materials are reviewed in a publication edited by Höcker et al. (Macromolecular Symposia, vol. 103, January 1996, Klee, D., Severich, B., Höcker, H., pp. 19–29). Among the most important present and future applications are fixation materials of different types for bone fracture treatment which can be used for manufacturing screws, nails or rods for the above mentioned application, just to mention an example. These materials can be either non-biodegradable ones, e.g., metals or metal alloys, or polymeric materials degradable at a controlled rate in the body.

The most widely used biodegradable materials are high molecular weight lactide homopolymers, and lactide copolymers with, for example, glycolide. Useful parts or products are processed from these materials with processing methods for thermoplastics known in polymer technology, such as injection molding, hot pressing or extrusion.

Dentistry is well familiar with polymeric materials, too. Typical polymeric dental filling materials are chemically (for example, photochemically) curable plastics based on methyl methacrylate, dimethyl acrylate and their derivatives.

Fixation bone cements for orthopedic hip prostheses are also based on monomer combinations methacrylate type. In these applications the curing is based on redox initiated free radical polymerization, and on thus accomplished cross-linking and network formation.

The methacrylate based implant materials are, however, neither biodegradable nor biocompatible to any particular extent, as Dr. Heikkilä reports in his dissertation (Annales Universitatis Turkuensis Ser. D: Medica-Odontologica, tom. 240, 23.8. 1996, Turku/Finland, Heikkilä, J., Bioactive glass as a bone substitute in experimental and clinical bone defects, pp. 1–97, especially on p. 30).

In the use of methacrylate based implant materials further problems are caused by the exposition of personnel to volatile compounds, and the heat released during the reaction which may lead to an excessive local temperature increase, and to tissue damages as a consequence.

Another application for synthetic implant materials is controlled release of drugs or other bioactive substances when the idea is that the potent agent is released at a controlled rate from the polymeric matrix. As an example of this kind of application one can mention Norplant, a product brand and a trade mark of Leiras Co., which is based on a non-degradable polymeric material. A definitely formed device is implanted into the body by a surgical operation, and it is removed therefrom in a similar manner after a defined time when the active component has been released and diffused to the body.

Specific needs for development in the present state of the art are connected to the following areas:

Biocompatibility

If the material is not biocompatible it may induce tissue inflammation, unwanted cell growth, or rejection. Biocompatibilities of the presently used bone cements based for the most part on poly(methyl methacrylate) are unsatisfactory. This causes a certain risk of loosening of the hip prosthesis even in the case that there exists connective tissue formation between the polymeric material and bone tissue. A better biocompatibility would be a significant benefit for these materials.

Bioactivity

A bioactive implant material makes possible an active interaction between the tissue and the implant. As an example can be taken a mechanism by which the tissue is enabled to reconstruct into the implanted material while the implanted material itself is gradually removed due to biodegradation. Heimke, G. and Griss, P. have in their publication (Tissue interactions to bone replacement materials, in Bioceramics of calcium phosphate, de Groot, K. (ed.), 1983, CRC Press, Boca Raton Fla., pp. 79–97) characterized the concept of bioactivity, and have been cited by Heikkilä in his publication (FIG. 1 in the publication cited on page 1 where a) bioincompatible materials, b) bioinert but by the interface biocompatible materials, and c) bioactive and biocompatible materials are presented schematically. In the case a) the implant is tolerated but no connection with bone is formed, in the case b) intimate contact without bone bonding occurs at the interface whereas in the case c) both intimate contact with chemical bone bonding and gradual transformation between bone and implant material will result).

Bioactive materials have scarcely been reported in the literature. Especially in the case of bone cements bioactivity would be desirable and a significant benefit.

Controlled Biodegradation

Depending on the application and purpose of implant materials, they are expected to have either long lasting durability or controlled degradability in the body at a predetermined rate to harmless degradation products. The wanted degradation rate is depending substantially on the renewal rate of the tissue. In the case of bone tissue, it may be case of several months, or even of a time span in the range of half an year to one year.

In the case of controlled drug delivery it is crucial what is the desired rate of release of the active ingredient from the biodegradable matrix. When the potent ingredient release is based on matrix degradation the rate of matrix degradation determines the release rate of the drug. When active agent is released from the matrix through diffusion, degradation of the matrix shall happen mainly only after the release of the active agent.

Industrial Hygienic Aspects

The materials in continuous clinical use have to be safe to the users in a sense of work safety and hygiene. This is a severe drawback with the present bone cements and dental filling materials based on methacrylates.

Controlled Mechanical Properties

The mechanical properties required from implant materials are depending on the application. With bone implants usually compression strength of at least 50 MPa is necessary, as well as bending strength and tensile strength values which reach the level of those of bone.

On the other hand, even in the bone applications, in case of bone grafting by filling of fractures and cavities, one can pretty well apply implant materials of lower strength if only the use properties, mouldability, biocompatibility, and possible biodegradability are at an optimum level.

In connection of soft tissue the requirement on the other hand is elasticity, flexibility and softness.

Plasticizability and Hardening Thereafter

The today used polymeric implant materials are either pieces of definite shape, i.e., processed before implanting to the final form using methods known in the plastics technology (as an example one can mention biodegradable bone nails based on polylactide, e.g., trade name Biofix), or bone cements based on methacrylate which typically have no biodegradability and lack bioactivity but as monomers, or as a blend of monomers, can be shaped in the target according to the needs, and can be hardened thereafter.

In surgery there would be plenty of applications for plasticizable, and afterwards to solid curable biodegradable polymeric materials. Then the idea is, that the material is plastic in connection to the surgical operation, and can be shaped according to the targets shapes or can be forced to penetrate even into small cavities, fractures and pores. Thereafter it again reversibly becomes solid, mechanically tough material having, however, the property of controlled degradation. Thus plasticizable material can be of the type of wax, plastics or rubber or even injectable viscous liquid.

Better biocompatibility, bioactivity and wished mechanical properties as combined to the mouldability in the target and hardening occurring thereafter are properties which before the present invention are described in a PCT application WO 98/26814.

Easiness of Application (Usability and Transferability to the Target)

The implant material is placed to the target in connection to a clinical situation, e.g., in connection to an operation. Then the applicability and the mouldability of the material has to be easy: it must be possible to, for example, inject it, or to place it with a special press, to the target, and its, hardening has to have a certain induction period during which the material can be shaped. On the other hand, one has to take into account that the possible drug present and/or the contact with tissue do not allow use of methods where the temperature even for a short period exceeds the typical upper limit of 55° C. The invention now present brings forward a novel solution significantly improving applicability of biodegradable implants, for example, in regenerating surgery and in long lasting drug therapy.

The Benefits of Porous Implant Materials

By using composites consisting of biopolymers and bioactive glass, there are indications that tissue regeneration has been achieved on the surface of the composites.

In applications where fast tissue regeneration is desired, for example reconstruction of bone defects, soft tissue defects and nerves, one has to achieve regeneration and bioactivity to occur in the whole implanted material, i.e. in the bulk of the material not only on the surface. This has not been possible to reach with the conventional composites of bioactive glass and biopolymers due to the fact that in these the bioactive glass is essentially covered by polymer layers, and bioactivity thus progresses gradually and incontinuously into the inner parts of the material, or this can occur first after the degradation of the biodegradable matrix.

Due to the above mentioned fact, it has been necessary to develop biopolymer materials which are porous thus having large surface area.

Production of Porosity

There are techniques described in the literature for the production of microscopic porous structures, or to achieve microscopic cavities into the synthetic polymeric materials aimed for the biomedical applications.

Literature knows methods, in which porosity is achieved through blending some water soluble solid material into the polymeric matrix, salt or saccharose being examples of the solid materials. Mikos et al. have published a paper in which biodegradable polylactide is produced to form porous structures by using sodium chloride as a porogen. Thus produced porous material is reported to be suitable for implant applications in tissue engineering.

In the article by Tsuji et al. there is described a composition, in which the porosity producing component is a water soluble polymer. One typical polymer which is water soluble and biocompatible is polyethylene oxide, i.e., polyethyleneglycol. This polymer has been blended with polylactide in a molten state and then a porous biomaterial is produced in aqueous conditions.

THE DESCRIPTION OF THE INVENTION

In comparison with the present state of the art, it has been possible according to the present invention surprisingly to achieve such a material, which enables the bioactivity throughout the whole implant, without the fact that the bioactive component would be surrounded by the polymeric matrix, thus reducing or preventing the bioactivity to the minimum. Furthermore one of the goals for the material according to the invention is to retain the possibility to plasticize it and its mouldability by hand or by using a specific tool or through injecting.

With surprise we have seen, that the above mentioned structure, and thus also the mentioned properties, by developing a processing method and a composition, in which a particle form bioactive component, which typically can be bioactive glass or hydroxyapatite, or even tissue fragments, just to mention some examples, has been placed into polymeric components in a way, that it remains into the cavities when the water soluble or fast degrading component is removed. Thus formed structure is presented in the FIG. 1.

Figure 1:
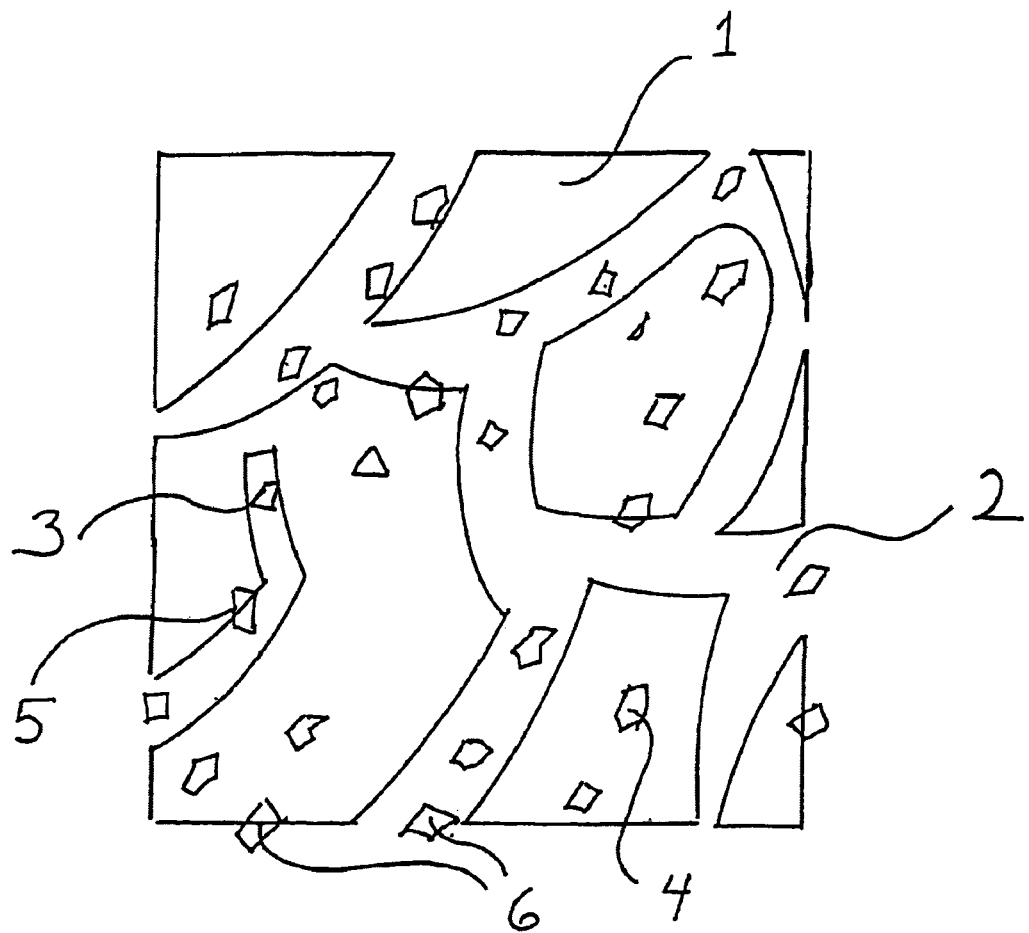
FIG. 1 is a drawing illustrating a structure of a biologically active material of the present invention.

In FIG. 1 there is the matrix polymer (1) into which an open porous structure (2) is formed after the removal of the soluble or fast degrading component. The third, bioactive and particle form component may locate either in the porous structures (3), in the matrix polymer phase (4), on the walls of the pores (5), or at the outer surfaces of the material (6).

The porous structure described above can be reached by using normal polymer blending methods, of which one can mention so called mixers of co-kneader type, twin screw extruders and static mixers. Also it is possible to blend polymeric solutions and further to evaporate the solvent.

The number and shape of the channels and pores thereafter is greatly dependent on the properties of the blended components, some of the most important ones being melt viscosity, blending conditions, and the volume proportions of the components in the blend. The channel structure formed through blending and other factors after that may greatly vary in its structure. The blending can be guided also in a way that a continuous penetrating network is achieved. The porosity of the material can be adjusted in wide ranges. According to the invention in the blending process a structure is formed in which the polymeric components form dispersed or interpenetrating phase structures.

In the material prepared with the method according to the invention the porous structure described above is formed through the degradation or solubilization of the channel forming component, as a result of that the material is in contact with water or fluids of the body. Thus functioning polymeric components are for example all water soluble polymers such as polyethylene oxide, polyethyleneglycols, polyvinylalcohols, and other polymers degrading hydrolytically relatively fast, such as several aliphatic polyesters, polyorthoesters, polyanhydrides and copolymers of these or polymers derived thereof, just to mention a few.

Furthermore it is characteristic of the materials composition prepared by using the method according to the invention that as a result of the channel and pore forming by water influence removing polymeric component blended with solid particles which induce or improve bioactivity or biocompatibility, the latter then will remain into the pores when the porogenic component has been removed with solubilization or degradation.

The concentration of the bioactive component in the porogenic material may vary in wide ranges. Even small concentrations improve bioactivity, and the upper limit is determined by the blending characteristics, according to our experience when the solid component concentration exceeds 75 wt-% in the blend. According to the invention it is desirable to blend the bioactive component as a separate operation to the porogenic component, and thereafter carry out the melt blending operation to form the interpenetrating or dispersed intermediate product, which is transformed into a porous structure, containing bioactive components in a favorable manner as a composition.

As one possible form of invention one can mention that the bioactive component, such as bioactive glass, is additionally or merely placed also into the matrix component in a separate blending procedure, so that it appears on the walls of the pores when the porogenic component then is removed through solubilization or degradation, and when the matrix itself is further degrading.

The matrix component may be either biodegradable or biostable according to the invention depending on the application and its demands. It can be provided with bioactivity with certain level by blending bioactive components in the same way as is the case with the porogenic component, and it may be connected with therapeutic substances. Suitable biodegradable matrix polymers are homo- and copolymers of lactones and polycarbonates, just to mention a few. It is of special advantage to use the polymers and compositions described in the patent publication WO 98/26814, so that the compositions according to this invention can be readily plasticized for moulding or even injected to a target.

Suitable biostable matrix polymers are derivatives of acrylic acid or methacrylic acid, just to mention a few, which as well known have a lot of applications in orthopedics and dentistry.

As a special benefit for the materials according to the invention are, that the bioactivity can be reached already by using small concentrations of the bioactive component in the porogenic component or/and in the matrix polymer. Thus the melt viscosity increase caused by large particles can be avoided. The material according to the invention can combine, if desired, easy mouldability, even injectability, and high, throughout the material extending bioactivity.

As the variations of the present invention the following combinations can be presented without being limiting the forms of implications:

Biostable matrix polymer and a water soluble polymer, in which there is a bioactive solid material Biostable matrix polymer, in which there is bioactive solid material and a water soluble polymer Biopolymer and a water soluble polymer, in which there is a bioactive solid material Biopolymer in which there is a solid component and a water soluble polymer Biopolymer and water soluble particles and a bioactive solid material The previous cases and in some or all components impregnated or blended active agent The previous cases in which there is instead of the water soluble component a fast degrading polymer The previous cases, and in them the water soluble or fast degrading polymeric component either as dispersed or continuous minority- or majority phase The previous cases, and in them the water soluble or fast degrading polymeric component distributed so that it forms a co-continuous interpenetrating segregation.

EXAMPLES 1–8

Polymerizations and Product Characterization

The Used Chemicals

The copolymers were prepared from $\epsilon$-caprolactone monomer ($\epsilon$-CL), >99% purity, Fluka Chemical, and D,L-lactide (D,L-LA), Purac. As catalyst was used tin(II)octoate (Stannous 2-ethylhexanoate; SnOct), 95% purity, Sigma. As the initiator was used glycerol, 99,5% purity, Fluka Bio-Chemical, and polyglycerol, having in average 8-OH groups (Daicel PGL06).

The Purification and Storage of the Used Chemicals

In the used $\epsilon$-caprolactone there was molecular sieves (adding date 15.02.1995), and the bottle was stored in a dark place at a temperature of 23° C. The caprolactone was not redistilled.

D,L-lactide was purified with recrystallization from toluene (b.p. 110° C.) using a mass ratio of 1:2 toluene/actide. The lactide dissolved to a hot toluene was poured from round bottom flask to a decanter. The lactide solubilized to the toluene was allowed to recrystallize overnight at 23° C. After filtration the crystallized lactide was dried under reduced pressure for 4 days at +40° C. and 4 mbar. The same stages were repeated once. In the polymerizations was thus used twice recrystallized D,L-lactide which was stored in an exiccator in a refrigerator at +4° C.

The tin octoate and the glycerol were used as such. They were stored in a dark place at +23° C.

Preparations for Polymerization

At preceding night the used lactide has been placed into a vacuum chamber at +40° C. and 4 mbar. The two-piece polymerization reactor (volume about 0.7 liter) was assembled, and the condition of the Teflon gasket belonging to the reactor was checked. The proper closure of the upper part and the lower part of the reactor was ensured by a iron wire closing device. The male parts of the glass joints belonging to the reactor were wiped slightly with vacuum grease.

Poly-D,L-lactide and poly-epsilon-caprolactone polymerizations were carried out batchwise in an agitated reactor of volume 2.5 liters, equipped with two intermeshing agitators, which create especially good agitation into the reaction mixture in every point of the conical reaction chamber.

Polymerization

The oil thermostat used for the reactor heating was regulated to 140° C. The oil temperature varies during a polymerization within 5° C. above and below the set temperature. Lactide was weighed first about 10 g into a small decanter (accuracy 0.0001 g). On the lactide the tin octoate and the glycerol was weighed using a Pasteur pipet. After this the decanter was poured into the reactor, and the rest of the lactide was weighed with another balance (accuracy 0.01 g). ϵ-Caprolactone was then either poured or pipetted on lactide.

The magnetic agitator has been added to the reactor before the reactor halves were closed. The reactor was placed into a thermostat, and the agitation was adjusted to the speed of 250 1/min. The reactor was flushed with Argon (AGA, grade S, 99.99%) for about 15 min. Argon was fed to the reactor through a glycerol trap. Finally the outside of the reactor was wrapped with aluminum foil. When the forming copolymer started to become more viscous the agitation speed was adjusted again to the speed of 125 1/min.

The Prepared Copolymers and Their Analysis

Table 1 summarizes the copolymerizations and their results using ϵ-caprolactone and D,L-lactide (ϵ-CL/D,L-LA), homopolymerizations of epsilon-caprolactone and the analysis results of the products. In all the polymerizations except example 18 the temperature was 140° C. and the polymerization time was 24 h (except in Example No. 3 where it was 29 h). In the homopolymerization runs of D,L-lactide and ϵ-caprolactone the temperature reached was 140° C. and the total polymerization time was 4 h. In the example 18 the temperature was 160° C. and polymerization time 4 h.

Molecular weights determined by gel permeation chromatography (GPC) are presented in Table 1 in terms of number average molecular weight Mn, weight average molecular weight Mw, and the polydispersity PD calculated as the ratio of the previous ones Mw/Mn. In the same Table 1 there are also presented the transition temperatures of the polymerization products, i.e. melting temperature Tm and glass transition temperature Tg, determined using differential scanning calorimetry (DSC).

TABLE 1

| Example | ϵ-CL D,L-LA- ratio (M-%) | SnOct- conc. mol/ mol · monomers | Glycerol conc. mol/ mol · monomers | GPC results | | | DSC results | |
|---|---|---|---|---|---|---|---|---|
| | | | | $M_n$ (g/mol) | $M_w$ (g/mol) | PD | $T_m$ (° C.) | $T_g$ (° C.) |
| 1 | 100/0 | 0.0001 | 0.005 | — | — | — | 56 | — |
| 2 | 80/20 | 0.0001 | 0.005 | 35000 | 50000 | 1.4 | 47 | — |
| 3 | 80/20 | 0.0001 | 0.005 | 40000 | 60000 | 1.5 | 42 | — |
| 4 | 80/20 | 0.0001 | 0.005 | 40000 | 60000 | 1.5 | 45 | — |
| 5 | 80/20 | 0.0001 | 0.0005 | 165000 | 272000 | 1.65 | 46 | −53 |
| 6 | 80/20 | 0.0001 | 0.25 | — | — | — | — | — |
| 7 | 100/0 | 0.0001 | 0.25 | 4300 | 5200 | 1.2 | 35 | — |
| 8 | 100/0 | 0.0001 | 0.05 | 445 | 729 | 1.6 | — | — |
| 9 | 100/0 | 0.0001 | 0.05 | — | — | — | — | — |
| 10 | 100/0 | 0.0001 | 0.25 | 2000 | 2600 | 1.3 | — | — |
| 11 | 100/0 | 0.0001 | 0.0125 | — | — | — | 53 | — |
| 12 | 100/0 | 0.0001 | 0.023 | 10000 | 12000 | 1.2 | — | — |
| 13 | 100/0 | 0.0001 | 0.034 | — | — | — | 43 | — |
| 14 | 80/20 | 0.0001 | 0.25 | 1100 | 1400 | 1.3 | — | — |
| 15 | 0/100 | 0.0002 | 0.0025 | 85900 | 106700 | 1.24 | — | 47 |
| 16 | 100/0 | 0.0001 | 0.01 | 17600 | 20900 | 1.18 | 46 | −64 |
| 17 | 0/100 | 0.0002 | 0.03 | 5100 | 6100 | 1.20 | — | 28 |
| 18 | 95/5 | 0.0002 | 0.0025 | 79300 | 137200 | 1.73 | 52 | −58 |

In the D,L-lactide polymerizations the batch size was 500 g D,L lactide catalyst concentration was 0.02 mol-% corresponding 0.295 g in the reaction mixture, and the initiator content when glycerol was used 0.25%, and when polyglycerol was used 3.0 mol-%, the amounts correspondingly in the reaction mixture 0,81 g and 48,8 g. The batch size in the epsilon-caprolactone polymerization was 1000 g, the catalyst concentration 0.01 mol-% corresponding 40.48 g in the reaction mixture. The monomers were weighted with an accuracy of 1 g, the catalyst and initiator with an accuracy of 0.001 g.

After the addition of the raw materials the reactor was flushed first with nitrogen (Aga, grade 99.999%) for 5 min and the reactor was closed. As the agitator speed 60 1/min was adjusted. The temperature of the reaction mixture was increased from room temperature (25° C.) to the level of 140° C. in 0.5 h, where after the agitation was continued at this temperature for 3.5 h.

GPC Measurements

The GPC-samples for molecular weight measurements were prepared by dissolution of 15 mg of sample into 10 ml of chloroform. As columns were used columns of Polymer Laboratories Ltd with pore diameters of 100–10 000 Å. The used detector was RI-, i.e., refractive index detector, manufactured by Waters, and a 55 min run time with a flow rate of 1 ml/min were used. To determine the molecular weights of the samples were used polystyrene (PS) standards manufactured by Polymer Laboratories, and the calibration curve based on the same. Because there is no experimental Mark-Houwink constants a and K available, the molecular weights in the Table 1 are not absolute molecular weights for the samples but relative values in comparison with PS standards.

DSC Measurements

DSC-measurements were carried out for the copolymer samples by using Polymer Laboratories PL DSC-device, and for the poly-ϵ-caprolactone and CL/DL-LA 95/5 copolymer by using Mettler Toledo Star DSC 821-device. In the DSC measurements the 5–10 mg sample was heated with a rate of 10° C./min in a calorimeter chamber. In order to get a similar thermal history for all the samples, the samples were heated above their melting temperature to temperature of +80° C. and cooled down to about −50° C. The Tm and Tg values were determined from the curve recorded from the second heating, and they are presented in the Table 1.

Preparation and Characterization of Biologically Active Polymer Blend

The Used Chemicals

As water soluble polymer in the preparation of biologically active polymer blends polyethylene glycol 20 000 of Fluka Chemicals was used, having melting point of 63–66° C. according to the manufacturer.

Polymers according to the experiments 18 and 19 in table 1 were used as biopolymers.

As biologically active component was used bioactive glass S53P4 of Abmin Technologies Company, having particle size 90–315 μm (examples 2–6) or 50–300 PM (examples 7–8).

DSC-Measurements

The thermal analyses were carried out by using Mettler Toledo Star DSC 821-equipment as previously described in connection with polymerizations, with the exception, however, that the sample was heated to +150° C. and cooled to −100° C.

Dynamic Measurements

Dynamic measurements were carried out by means of a cooled controlled dynamic rheometer. RSI-Orchestrator—program was used to process the results. The measurements were carried out by using pellet form samples which were elongated from melt before the test runs. The distance of the measuring heads was set to be 1.0 mm.

The measurements were started with a stress sweep, in which a variable stress was applied into the sample to determine a region of linear viscoelasticity (LVE). The linear viscoelasticity is valid when the deformations produced into the material are indefinitely small and the material deviates from the equilibrium just insignificantly or the deformation is very slow. Based on this the suitable strain for the frequency sweep was selected. The frequency sweep was carried out in the frequency sweep of 0.1–100 rad/s, and in addition the first point of the frequency sweep was repeated. Based on the measurements a rough estimate of the viscosity level of the blend components was gained. The dynamic viscosities eta* are presented in the table 2.

TABLE 2

| Sample | Eta* (Pa s) |
|---|---|
| PEG 20000 | 20 |
| PEG 20000: S53P4, weight based blend ratio 50:50 | 80 |
| PEG 20000: S53P4, weight based blend ratio 70:30 | 250 |
| P (CL95/DL-LA5) | 1200 |

The viscosity level of the blends of bioactive glass and polyethylene glycol was in other words in all the examples significantly lower than that of the biopolymer. In polymer science it is known the phenomenon that the lower viscosity forming blend component tends to form the continuous phase, although the other component would have a larger volume fraction. Based on the previous fact it is apparent that in the compositions according to the examples 1 and 2–5 porosity is formed due to cavities and web like channels when the PEG is dissolved into water.

Measurements of Densities

The changes of the densities of compositions were investigated by using Sartorius densitometer YDK 01. The measurement is based on the lifting force in the solid sample immersed into the liquid. By weighting the solid material both in the air and in the liquid, the density of which is known at measurement temperature, the density of the solid material can be determined according to the equation (1):

$$\rho = (W(a) \times \rho(fl))/(W(a) - W(fl)) \qquad (1)$$

where $W(a)$=weight of the solid material in air $W(fl)$=weight of the solid material in liquid $\rho(fl)$=liquid density at measuring temperature.

In the density measurements distilled water was used as the liquid, at a temperature of 23.1° C. during the measurements. The measurements were carried out by using specimens dried to a constant weight. Because there was a variable and limited amount of repeated experiments, the accuracy of the results was decided to be two decimals.

Example 1

Blending of Biopolymer and Polyethylene Glycol

The blend of polycaprolactone (PCL) and water soluble polyethylene glycol (PEG 20 000, Fluka Chemika) was prepared in a Brabender melt mixer W 50 EH attached to Plasticorder PLE 661 rheometer, so that into the mixing chamber, having volume of 50 milliliters and set temperature 80° C., both components were added equal amounts volumetrically. During 60 1/min, and agitation was continued for 5 min. Thereafter the blend was removed as a melt from the mixer and it was used to prepare specimens.

Example 2

Blending of the Polyethylene Glycol and Bioactive Glass

Commercially available bioactive glass S53P4, having particle size 90–315 μm, was blended 25 g with an equal amount of polyethylene glycol by using the conditions described in the example 1. A light composite was removed from the melt mixer for rotational rheometry and DSC-runs.

Example 3

Blending of Biopolymer with the Blend of Polyethylene Glycol and Bioactive Glass 20 g of composite material based on bioactive glass and polyethylene glycol prepared according to example 2 was blended with 30 g of biopolymer, which in this example was a copolymer of ε-caprolactone and D,L-lactide, i.e. P(CL95/DL-LA5), in which the molar ratio of monomers was 95:5. The melting point of the copolymer determined by DSC was around 50 C. The melt blending was carried out according to the blending conditions according to the example 1.

Example 4

Blending of Biopolymer with a Blend of Polyethylene Glycol and Bioactive Glass in a Reverse Order in Comparison with the Previous Example The blending of the polyethylene glycol and bioactive glass was carried out as is described in the example 2. In the second stage 30 g of the mentioned composite and 20 g of biopolymer were blended P(CL95/DL-LA5). The melt blending was carried out in blending conditions described in connection with the earlier experiments.

Example 5

Blending of Biopolymer into the Blend of Polyethylene Glycol and Bioactive Glass when the Blend Rati is Different in Comparison with the Previous Example 35 g of bioactive glass and 15 g of polyethylene glycol were blended as is described in the example 2. Granular composite material was removed from the melt mixer and it was characterized by using rotational rheometry and DSC-calorimetric runs. In the second stage was melt blended 30 g composite material consisting of bioactive glass and polyethylene glycol, prepared according to example 1, and 20 g of biopolymer P(CL95/DL-LA5).

Example 6

Preparation of Specimens and Their Hydrolysis

The blends according to 1 and 2–5 were compression molded by using Fontijne TP 400-table press at 80° C. to specimens with dimensions of 2*4*20 mm. The specimens, weighing 160–240 mg, were immersed into test tubes containing 10 ml distilled water each. The test tubes were sealed with caps and placed into holders in shaking baths, having speed of 30 1/min and temperature 37° C. After certain intervals three parallel samples were removed for weighing. The removed specimen were rinsed with distilled water, surface dried and weighed, afterwards they were let to dry in a vacuum chamber until they reached constant weight, i.e. about 5 d. The water absorptions (wt-%), and relative mass losses (wt-%) are shown in table 3.

TABLE 3

| Sample | Hydrolysis time (d) | Absorption (wt %) | Mass loss (wt-%) |
| --- | --- | --- | --- |
| Example 1 | 1 | 36 | 25 |
| Example 1 | 7 | 52 | 35 |
| Example 1 | 24 | 52 | 36 |
| Example 1 | 50 | 46 | 37 |
| Example 3 | 7 | 26 | 16 |
| Example 3 | 15 | 26 | 18 |
| Example 4 | 7 | 22 | 28 |
| Example 4 | 15 | 22 | 29 |
| Example 5 | 7 | 20 | 15 |
| Example 5 | 15 | 21 | 16 |

Figure 2:
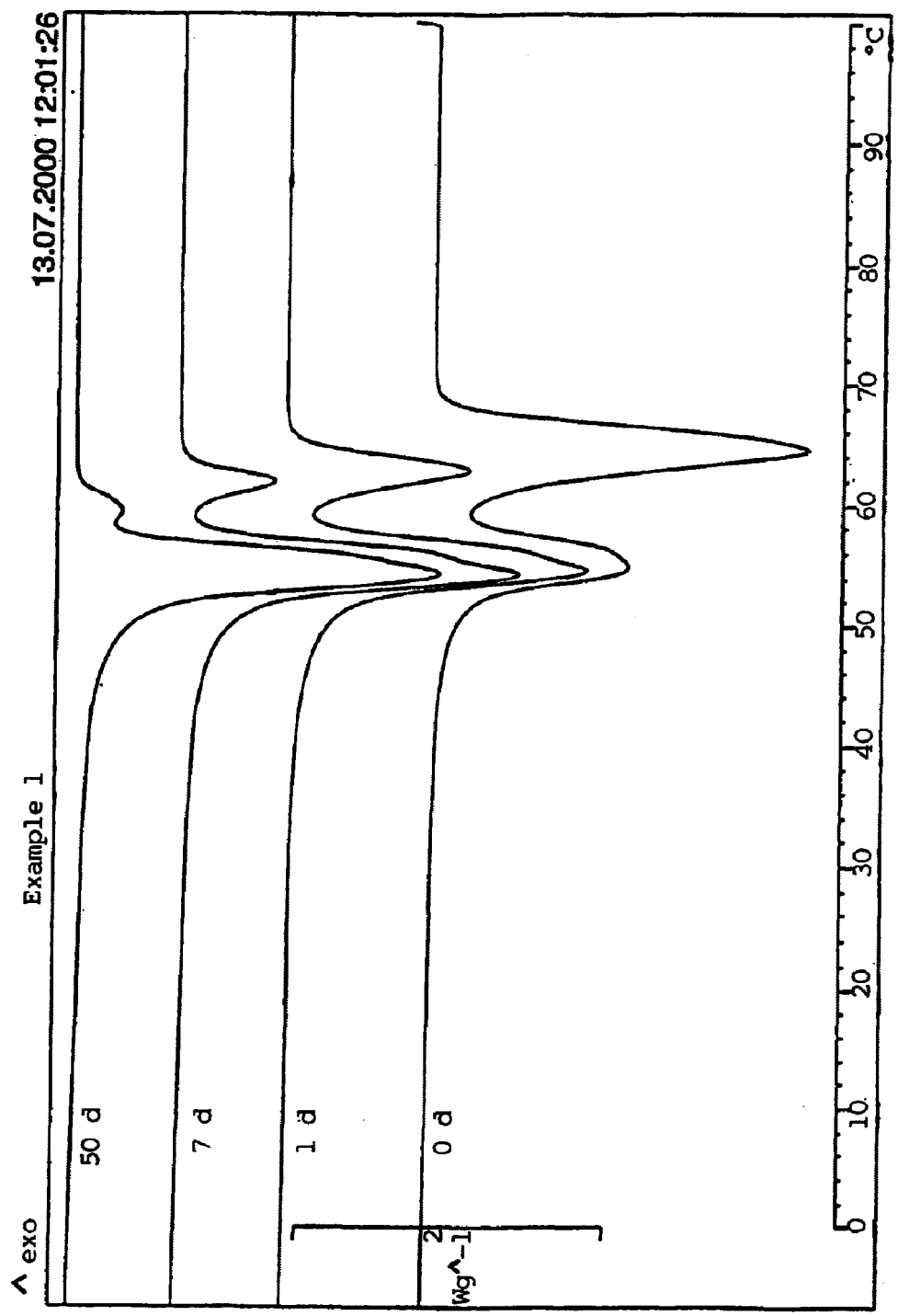
FIG. 2 shows DSC curves for a specimen of a biologically active material prepared from a blend according to Example 1.
Figure 3:
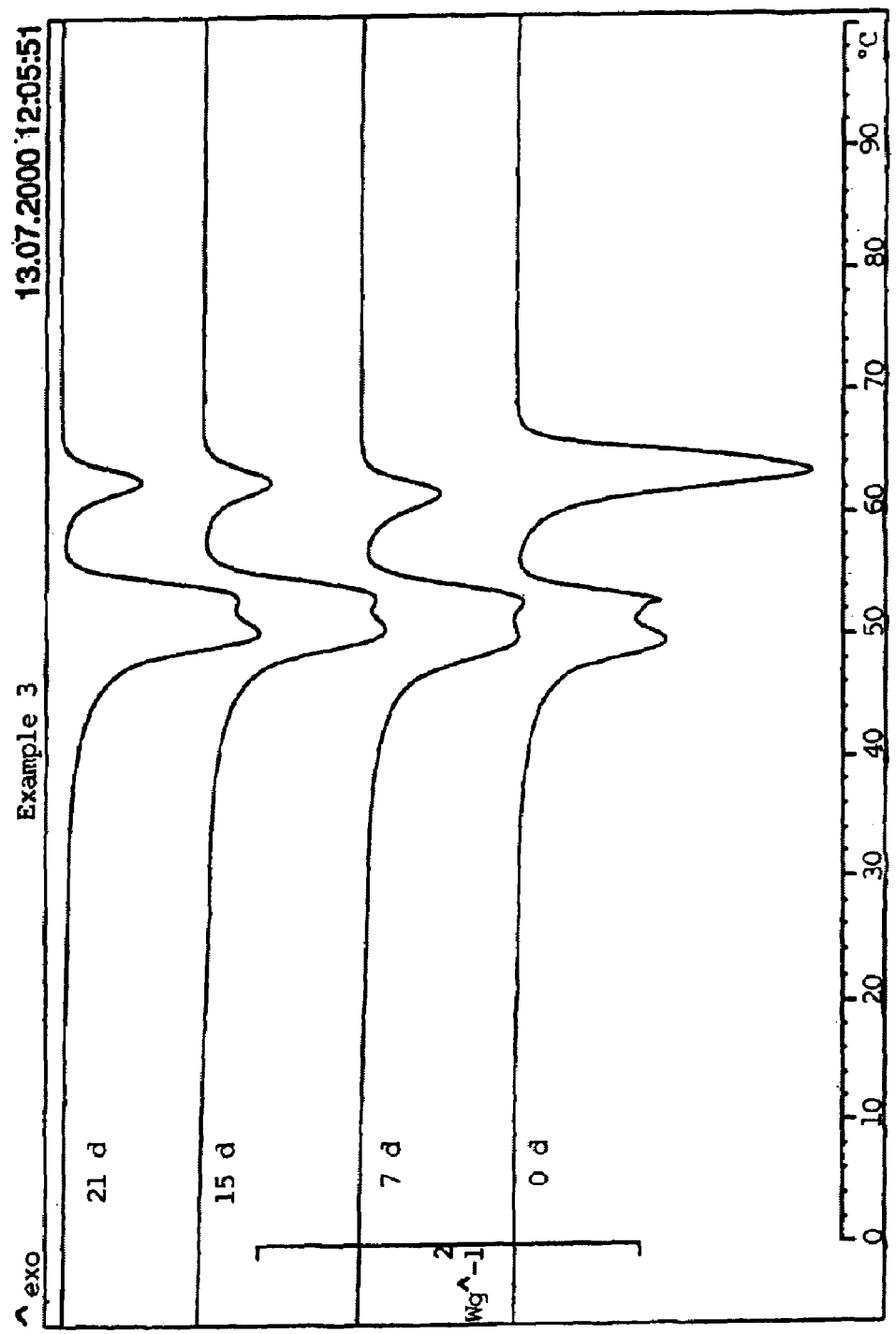
FIG. 3 shows DSC curves for a specimen of a biologically active material prepared from a blend according to Example 3.

The up to the constant weight weighed specimens were analyzed by DSC, and based on the results the diminishing of the polyethylene glycol fraction in the composite with the hydrolysis time could be followed. FIG. 2 presents DSC curves for specimen prepared from a blend according to example 1 in a couple of time points. FIG. 3 presents corresponding DSC-curves for example number 3. The generation of porosity in the material was followed indirectly through the density changes observed in the material.

According to the weighing results there was a significant weight loss (around 25 wt-%) of the specimens already after hydrolysis time of 24 hours. In the density measurements the blend was observed to have changed lighter than water (before hydrolysis the specific gravity was around 1.1 g/cm$^3$).

After one week the mass loss in for the blend was up to 35 wt-%. The weight loss can mainly be due to the extraction of polyethylene glycol into the water, because correspondingly from polycaprolactone prepared and hydrolyzed reference specimens did lose weight only 0.2 wt-% in the same time. In addition, DSC-curves shoved for the blends a typical endothermic melting peak of PEG, the height of which, however, was significantly reduced due to the hydrolysis.

The weight loss for the composition according to the example 3 was 16 wt-%. The density reduced correspondingly from 1.27 g/cm$^3$ to 1.19 g/cm$^3$: DSC—curve indicated reduction of the endothermic melting peak of polyethylene glycol when one compares curves of hydrolyzed and non-hydrolyzed samples.

The weight loss for the composition according to example 4 was 28 wt-% in one week hydrolysis. The density was correspondingly reduced from its initial value 1.34 g/cm$^3$ to the value of 1.09 g/cm$^3$. In the DSC-curve the endothermic melting peak due to polyethylene glycol was, however, still detectable.

In the extraction experiment the bioactive glass component essentially did not leach out from the test specimens but the glass particles remained into the formed pores.

The material according to the example 3 was investigated by using microtomography. A continuous phase structure was formed.

Example 7

Production of Porosity by Using Sodium Chloride

A 50/50 wt-% solid particle mixture was prepared by using particle form sodium chloride (NaCl) and bioactive glass with particle size of 50–300 μm. Two thirds of a test tube was filled with this mixture of solid particles. In the next stage the empty spaces between the particles were filled with a liquid methacrylate type of monomer with a thermal initiator. The liquid monomer was polymerized by heating the test tube in a water bath at 70° C. for three hours. A hard material was obtained, and it was removed from the test tube. The rod thus produced was cut into 3 mm*3 mm*5 mm rods which were weighed. Then the rods were placed into water for 3 days, after what they were dried and weighed again. The weight change indicated the formation of porous structure due to the dissolution of NaCl-component into the water. No detection of leached glass component was done, the glass component remained into the pores and on their walls. The porous structure was confirmed by microscope. In vivo experiments indicated bioactivity.

Example 8

Production of Porosity by Using Sugar

A mixture according to the previous example was prepared so, however, that the soluble component was sugar. The formation of porous structure was observed.

The invention claimed is:

1. A method of producing a heterophasic implant material through blending three components A, B and C, which are essentially immiscible with each other and wherein A is a bio-compatible plastic, B is a water-soluble or hydrolytically degrading polymer, and C is a particle-formed bioactive substance, characterized by blending component C into component A or component B, or into both of these, to obtain a heterophasic mixture, and then blending components A and B with each other by melt-blending to provide form dispersed or interpenetrating phase structures of the polymeric components, and subsequently removing component B from the heterophasic mixture through immediate or gradual solubilization or degradation so that the particles of bioactive component C remaining or being revealed can be contacted with living tissue.

2. A method according to the claim 1, characterized in that component B is removed during the production process of the bioactive implant material to form a channel or network structure in component A.

3. A method according to the claim 1, characterized in that component B is removed by the solubilization of body fluids.

4. A method according to the claim 1, characterized in that component C is blended into component B or into both component A and component B.

5. A method according to the claim 1, characterized in that component A is a body compatible thermoplastic, selected from derivatives of methacrylic acid, acrylic acid and vinylpyrrolidone, polyolefins, polylactones, polycarbonates, polyanhydrides, polyorthoesters, and copolymers of the above mentioned, and polymers and copolymers based on units derived from hydroxyacids.

6. A method according to the claim 1, characterized in that component A is a thermoset based on a prepolymer or monomers which can be hardened by curing.

* * * * *